(12) United States Patent
Li et al.

(10) Patent No.: US 9,798,858 B2
(45) Date of Patent: Oct. 24, 2017

(54) METHOD AND SYSTEM FOR AUTOMATICALLY EVALUATING THE QUALITY OF MEDICAL RECORDS

(75) Inventors: Bo Li, Beijing (CN); Xue Qiao Hou, Beijing (CN); Hui-I Hsiao, San Jose, CA (US); Gang Hu, Beijing (CN); Yue Pan, Haidian District (CN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 2161 days.

(21) Appl. No.: 12/430,348

(22) Filed: Apr. 27, 2009

(65) Prior Publication Data
US 2009/0281837 A1 Nov. 12, 2009

(30) Foreign Application Priority Data
Apr. 28, 2008 (CN) .......................... 2008 1 0091269

(51) Int. Cl.
  *G06F 19/00* (2011.01)
  *G06Q 50/22* (2012.01)
  *G06Q 50/24* (2012.01)
(52) U.S. Cl.
  CPC .......... *G06F 19/324* (2013.01); *G06Q 50/22* (2013.01); *G06Q 50/24* (2013.01)

(58) Field of Classification Search
  CPC .......... G06Q 50/22; G06Q 50/24; G06F 17/27
  USPC ........................................... 705/2–3; 707/739
  See application file for complete search history.

(56) References Cited

U.S. PATENT DOCUMENTS

| | | | |
|---|---|---|---|
| 5,307,262 A | 4/1994 | Ertel | |
| 6,778,703 B1 | 8/2004 | Zlotnick | |
| 7,260,568 B2 * | 8/2007 | Zhang | G06F 17/30663 707/711 |
| 7,610,192 B1 * | 10/2009 | Jamieson | G06F 17/2229 704/1 |
| 2004/0243614 A1 | 12/2004 | Boone | |
| 2006/0155699 A1 | 7/2006 | Purvis | |
| 2007/0150314 A1 | 6/2007 | Abraham-Fuchs | |

* cited by examiner

*Primary Examiner* — Joy Chng
(74) *Attorney, Agent, or Firm* — Tutunjian & Bitetto, P.C.; Rabin Bhattacharya (57) ABSTRACT

A method, a system, and a computer readable article of manufacture tangibly embodying computer readable instructions for executing a computer implemented method for automatically evaluating the quality of a medical record. The method includes: generating temporary facts from a medical record to be evaluated; constructing a query to a knowledge base of standard facts of standard medical records from the temporary facts; executing the query to the knowledge base by using a reasoning engine; and determining the quality of a medical record to be evaluated based on the result of the query.

17 Claims, 11 Drawing Sheets

METHOD AND SYSTEM FOR AUTOMATICALLY EVALUATING THE QUALITY OF MEDICAL RECORDS

CROSS-REFERENCE TO RELATED APPLICATION

This application claims priority under 35 U.S.C. §119 from Chinese Patent Application No. 200810091269.X filed on Apr. 28, 2008, the entire contents of which are incorporated herein by reference.

BACKGROUND OF THE INVENTION

Field of the Invention

The present invention relates to the computer field, particularly to the field of semantic network and artificial intelligence, and more particularly to a method and system for automatically evaluating the quality of a medical record.

Description of Related Art

A medical record is a systematic documentation of a patient's medical and care history. Medical record drafting refers to the behavior of a health care provider obtaining related material by medical activities such as interrogation, physical examination, auxiliary examination, diagnosis, treatment and nursing, and forming medial activities documentation through induction, analysis and collation of the material. Medical records play an important role in medical activities.

The information contained in a medical record enables health care providers to provide continuous care to the patient. A medical record also serves as a basis for planning the patient's care, documenting communications between the health care provider and other health professionals contributing to the patient's care, assisting in protecting the legal interests of the patient and health care providers responsible for the patient's care. In addition, medical records can also serve as documents to educate medical students/resident physicians, to provide data for hospital internal auditing and quality assurance, and to provide data for medical research. So the quality of medical records drafted by health care providers is very important.

In current medical practices, precision and completeness of a medical record are two most important criteria for evaluating the quality of the medical record, and are also the most principal quality issues in the drafting of a medical record. Precision and completeness of a medical record have the meanings which follow.

For a certain section of a medical record with a given type, the statements should be complete. For example, the physical examination content of a clinic medical record should include body temperature, respiration and sphygmus. The statements should be as specific as possible. For example, it should be "having had a fever for 3 days" instead of "having a fever." The statements should be in a certain sequence. For example, the correct sequence of physical examination is temperature, sphygmus and respiration.

Correct terms should be used. For example, a symptom statement should be used in a chief complaint instead of a disease class as far as possible, such as "chief complaint: having had a fever for 3 days" instead of "chief complaint: upper respiratory tract infection." Formal vocabulary should be used, such as "diarrhea" instead of "having loose bowels."

In current medical practices, the evaluation of the quality of a medical record is performed by an evaluation person through human judgment based on formulated evaluation criteria for the quality of a medical record. Not only this kind of human judgment method need to consume a lot of time and manpower, but also it is difficult for the method to provide an objective and precise evaluation for the quality of a medical record. In addition, the human judgment method is mainly used for checking the completeness of a medical record and is difficult to be applied to check the precision of a medical record.

Thus, in the art there exists a demand for a method and system for automatically evaluating the quality of a medical record by using a computer.

SUMMARY OF THE INVENTION

In order to solve the defects of the manual method for evaluating the quality of a medical record in the prior art, there is provided a method and system for automatically evaluating the quality of a medical record.

According to an aspect of the present invention, there is provided a method for automatically evaluating the quality of a standard document. The method includes: providing a knowledge base of standard facts of standard documents; generating temporary facts from the standard documents; constructing a query to the knowledge base from the temporary facts; executing the query by a reasoning engine; and determining the quality of the standard document to produce an evaluation result based on the query.

According to another aspect of the present invention, there is provided a system for automatically evaluating the quality of a standard document. The system includes: a fact generator for generating temporary facts from a document to be evaluated; a query constructor and executor for constructing a query to a knowledge base of standard facts of standard documents from the temporary facts; a reasoning engine for executing the query to the knowledge base; and a query result processor for determining the quality of the document to be evaluated based on the result of the query.

In yet another aspect, the present invention provides a computer readable article of manufacture tangibly embodying computer readable instructions for executing a computer implemented method for automatically evaluating the quality of a standard document by a computer. The method includes: providing a knowledge base of standard facts of standard documents; generating temporary facts from the standard documents; constructing a query to the knowledge base from the temporary facts; executing the query by a reasoning engine; and determining the quality of the standard document to produce an evaluation result based on the query.

BRIEF DESCRIPTION OF THE DRAWINGS

The attached claims describe novel features believed to be characteristic of the present invention. However the invention itself and its preferred embodiments, additional objects and advantages can be best understood from the following detailed description of the illustrative embodiments when read in conjunction with the drawings.

FIGS. 2 (a), 2 (b) and 2 (c) show a unified medical record model used in an embodiment of the present invention.

DETAILED DESCRIPTION OF THE PREFERRED EMBODIMENTS

Embodiments of the present invention will be explained below. However it should be understood that the present invention is not limited to the embodiments described here. On the contrary, it is contemplated to implement or practice the present invention by using any combination of the following features and elements, regardless of whether they involve different embodiments. Therefore, the following aspects, features, embodiments and advantages are only used for illustration and should not be regarded as elements or definitions of the attached claims, unless indicated otherwise explicitly in the claims.

The advantages of the present invention include the following:

The system automatically evaluates the quality of a medical record, which saves manpower and time, enhances the ability for evaluating the correctness of a medical record, and avoids the influences of subjective factors in a manual evaluation;

It is declarative rule based, and thus is user friendly and easy to be extended and enhanced;

It is subject to rule based matching, and thus can not only identify mismatches with a standard pattern, but also can output the differences between the standard pattern and the medical record to be evaluated; and It leverages existing knowledge in a terminology system to format concepts and subsumption relations, and thus only needs relatively small effort in knowledge engineering.

Figure 1:
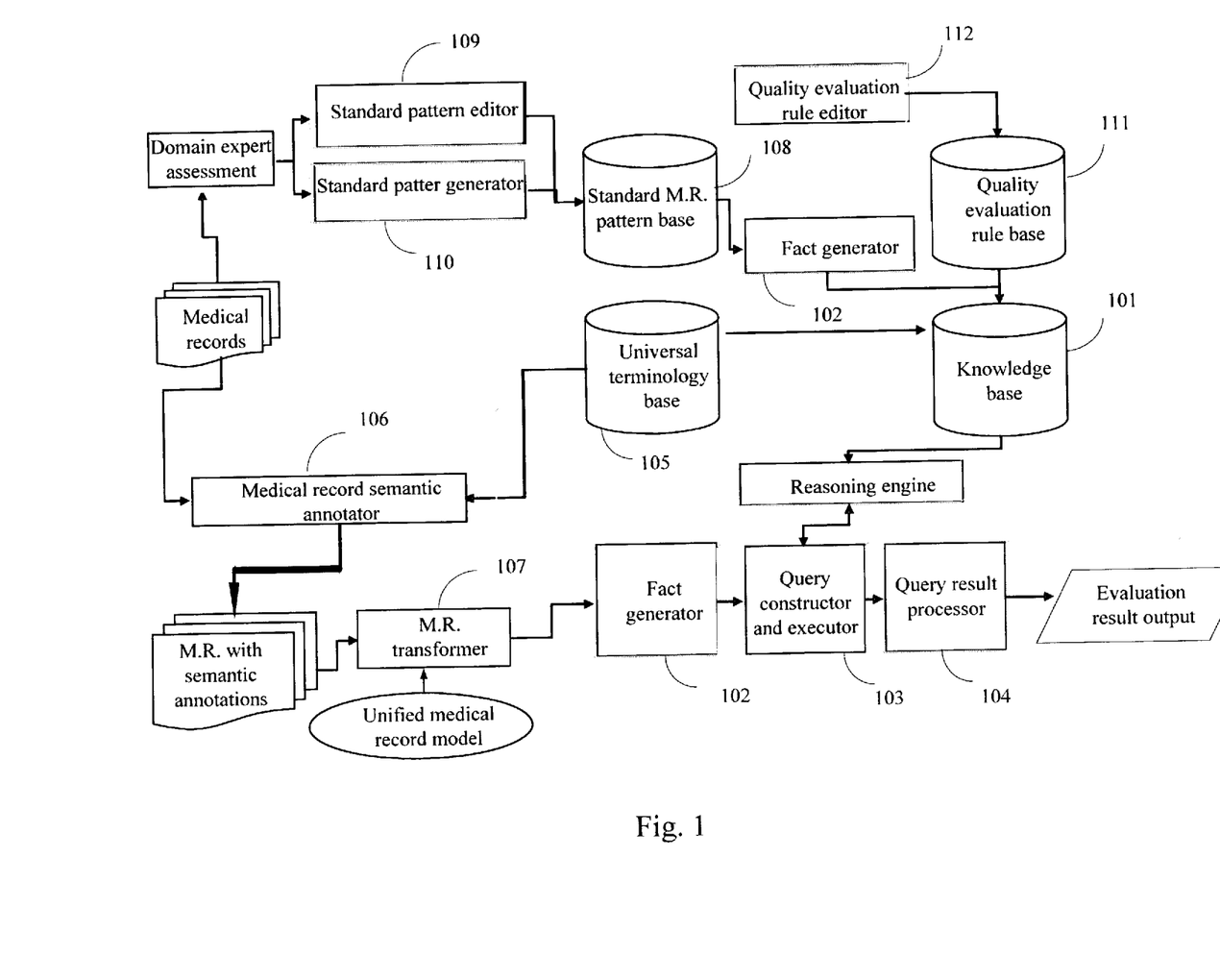
FIG. 1 shows a system for automatically evaluating the quality of a medical record according to an embodiment of the present invention.

FIG. 1 shows a system for automatically evaluating the quality of a medical record, M.R., according to an embodiment of the present invention. As shown in the figure, the system includes a knowledge base 101 containing standard facts of a standard medical record; a fact generator 102 for generating temporary facts from a medical record to be evaluated; a query constructor and executor 103 for constructing a query to the knowledge base from the temporary facts, and executing the query to the knowledge base through a reasoning engine; and a query result processor 104 for determining the quality of the medical record to be evaluated based on the results of the query.

The knowledge base 101 stores facts regarding medical terms and relations from a universal terminology base 105, quality evaluation rules from a quality evaluation rule base 111, and standard facts generated by the fact generator 102 based on a standard medical record pattern.

The universal terminology base 105 is a terminology system for medical records, and contains a vocabulary of narrative content in medical records and the semantic relations among the terms, such as generic/specific relations in clinic concepts. It can be either an existing terminology system such as SNOMED, LOINC or LCD, or a newly developed terminology system such as a traditional Chinese medical terminology system.

In an embodiment of the present invention, the system further includes a standard medical record pattern base 108 for storing various types of standard medical record patterns, so that the fact generator 102 can generate standard facts based on the standard medical record patterns in the standard medical record pattern base 108, for example, the section of "physical examination" must contain statements on "head, neck, chest, . . . ," and so on.

The standard medical record patterns in the standard medical record pattern base 108 can either be edited and stored in the standard medical record pattern base 108 by a domain expert using a standard pattern editor 109 according to an embodiment of the present invention, or be generated automatically by a standard pattern generator 110, according to an embodiment of the present invention, from standard medical records approved by a domain expert. The standard pattern generator 110 can generate standard medical record patterns from standard medical records by using methods known in the art. In an embodiment of the present invention, the data structure of the standard medical record pattern conforms to the unified medical record model, and the semantic terminology thereof conforms to the universal terminology base 105.

In an embodiment of the present invention, the system further includes a quality evaluation rule base 111 for storing various quality evaluation rules relevant to the evaluation of the quality of a medical record, and providing them to the knowledge base 101. The quality evaluation rules in the quality evaluation rule base 111 can either be edited by a domain expert and stored in the quality evaluation rule base 111, or be generated automatically by a quality rule generator from standard medical record patterns and stored in the quality evaluation rule base 111. The quality evaluation rules in the quality evaluation rule base 111 can be extended, changed and enhanced by a user at any time. In some embodiments of the present invention, the system can also not include the quality evaluation rule base 111, but can store quality evaluation rules as standard facts into the knowledge base 101 directly.

The quality evaluation rules, as standard facts and rules, use declarative rules to represent quality evaluation criteria, and contain some pre-defined rules for evaluating the quality of a medical record, such as the recursive rule for the predicate "FollowedBy", as it has transitivity.

In an embodiment of the present invention, the system further includes a medical record semantic annotator 106 for providing semantic annotations to a medical record to be evaluated, thus generating a medical record with semantic annotations. The medical record semantic annotator 106 can provide semantic annotations to a medical record to be evaluated by using semantic annotation methods known in the art, and preferably using the universal terminology base. In some embodiments of the present invention, the medical record semantic annotator 106 can be excluded, and a medical record with semantic annotations can be generated from a medical record to be evaluated by using a manual semantic annotation method.

In an embodiment of the present invention, the system can further include a medical record transformer 107 for transforming a medical record to be evaluated into an instance of the unified medical record model. The unified medical record model refers to the data model representing a schema model and a semantic model of a medical record. The model can be customized and extended as required. A typical and common implementation of the model is HL7 CDA R2, which is an ANSI standard. Here, HL7 is Health Level 7, CDA is Clinical Document Architecture. The generated unified medical record model instance contains document schema elements such as sections, entries and terms, and indicates semantic attributes of the terms and semantic relations among the terms.

Figure 2:
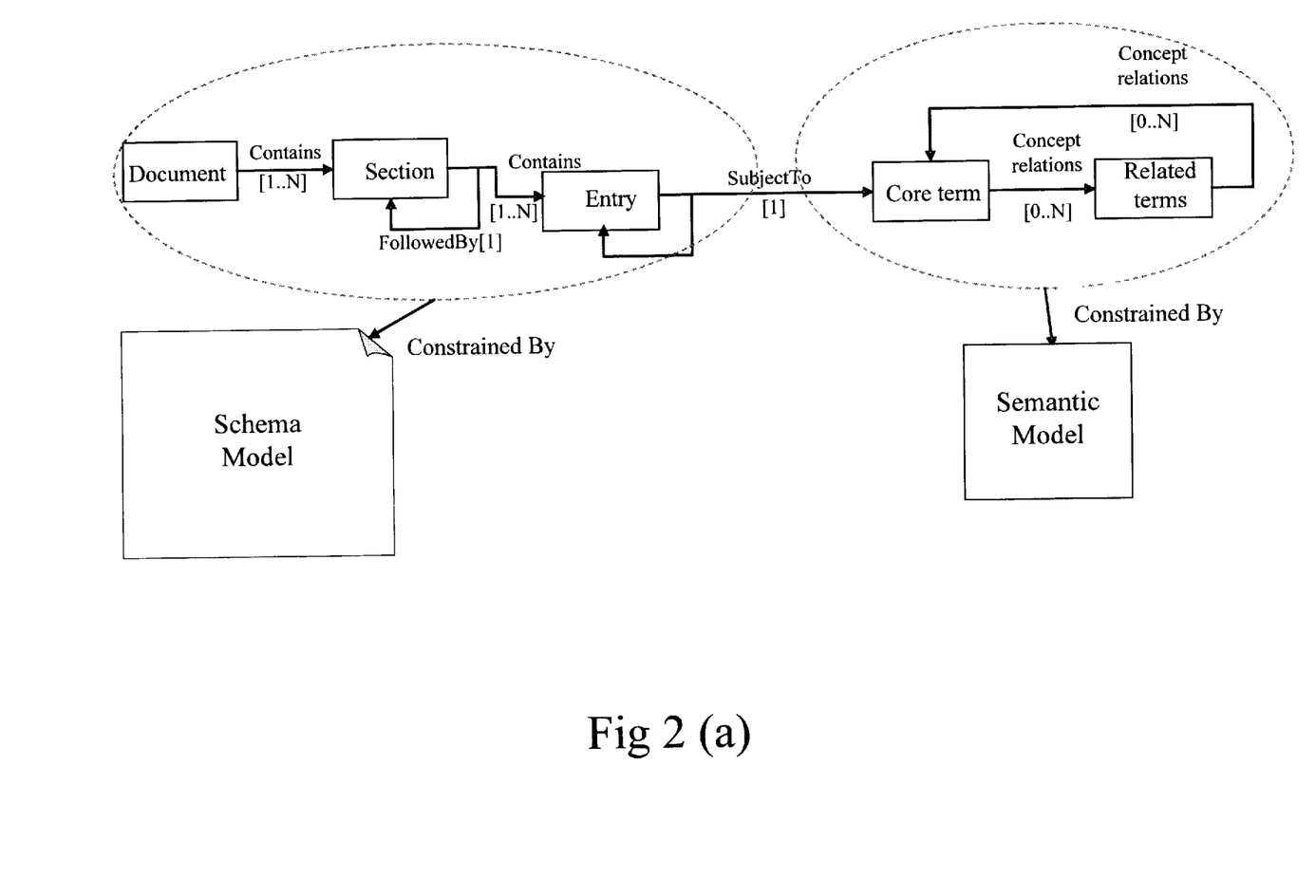

FIG. 2 (*a*) shows the unified medical record model. As shown, the unified medical record model is constrained by a schema model on one hand, and by a semantic model on the other hand. The schema model, FIG. 2 (*b*), defines the document structure of a medical record, where a medical record document contains one or more sections, the sections having sequence relationships; each section has one or more entries, each of which contains one or a set of semantically independent statements; the one or set of statements relate to a core term and a plurality of related terms. The semantic model, FIG. 2 (*c*), defines the semantic relations between the core term and the related terms in each entry.

Figure 3:
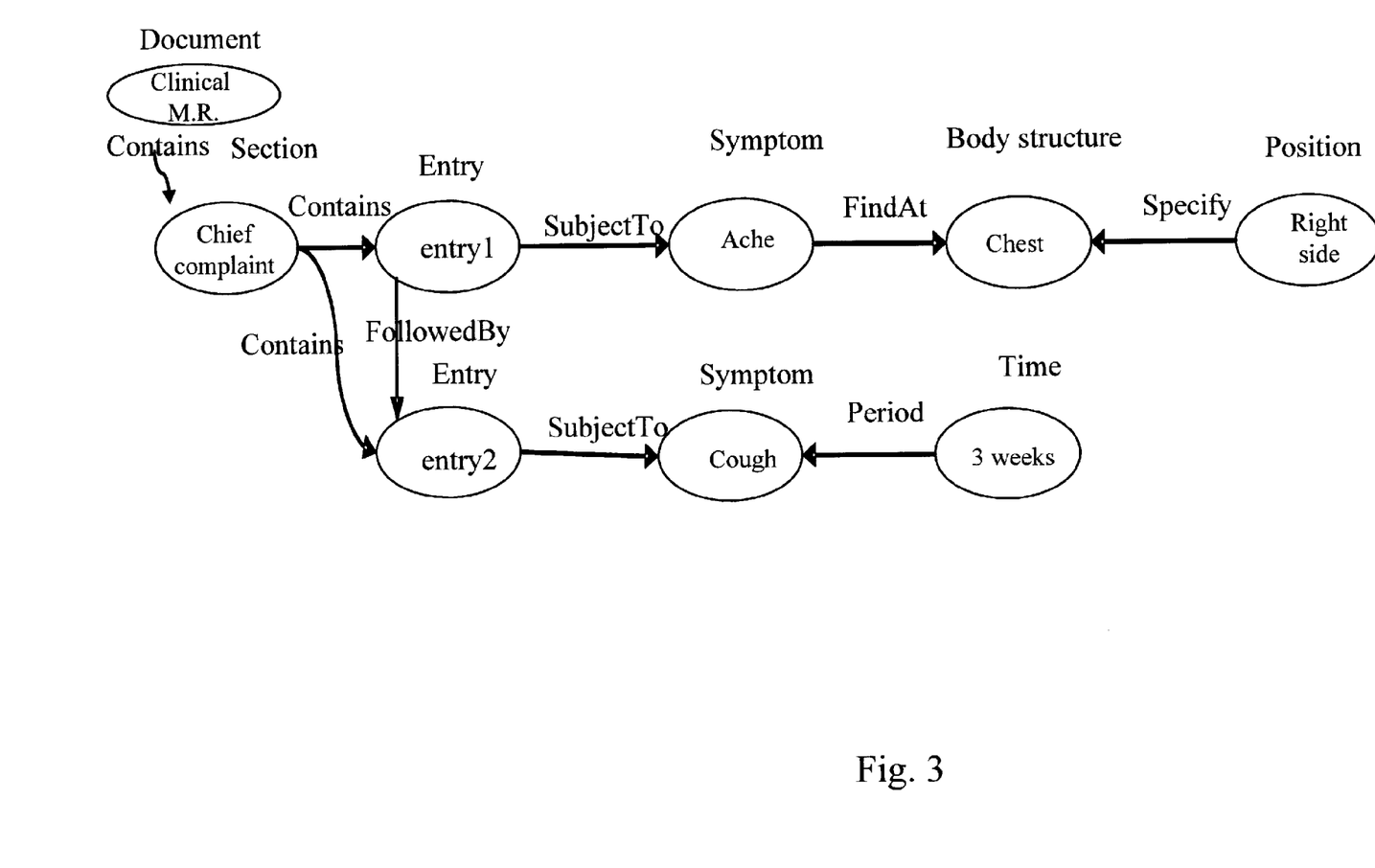
FIG. 3 shows a unified medical record model instance generated from a section of an exemplary medical record based on a unified medical record model according to an embodiment of the present invention.

FIG. 3 shows a unified medical record model instance generated from a section of an exemplary medical record, according to the unified medical record model, the text description of the section of the exemplary medical record being "chief complaint: having an ache at the right side of the chest and having been coughing for 3 weeks". The generated united medical record instance contains a chief complaint which contains two entries in sequence, the first entry relating to a core concept "ache" and related concepts "chest" and "right side", and the second item relating to a core concept "cough" and a related concept "three weeks".

As mentioned above, the fact generator 102 can either generate standard facts from a standard medical record pattern, or generate temporary facts from a medical record to be evaluated.

Figure 4:
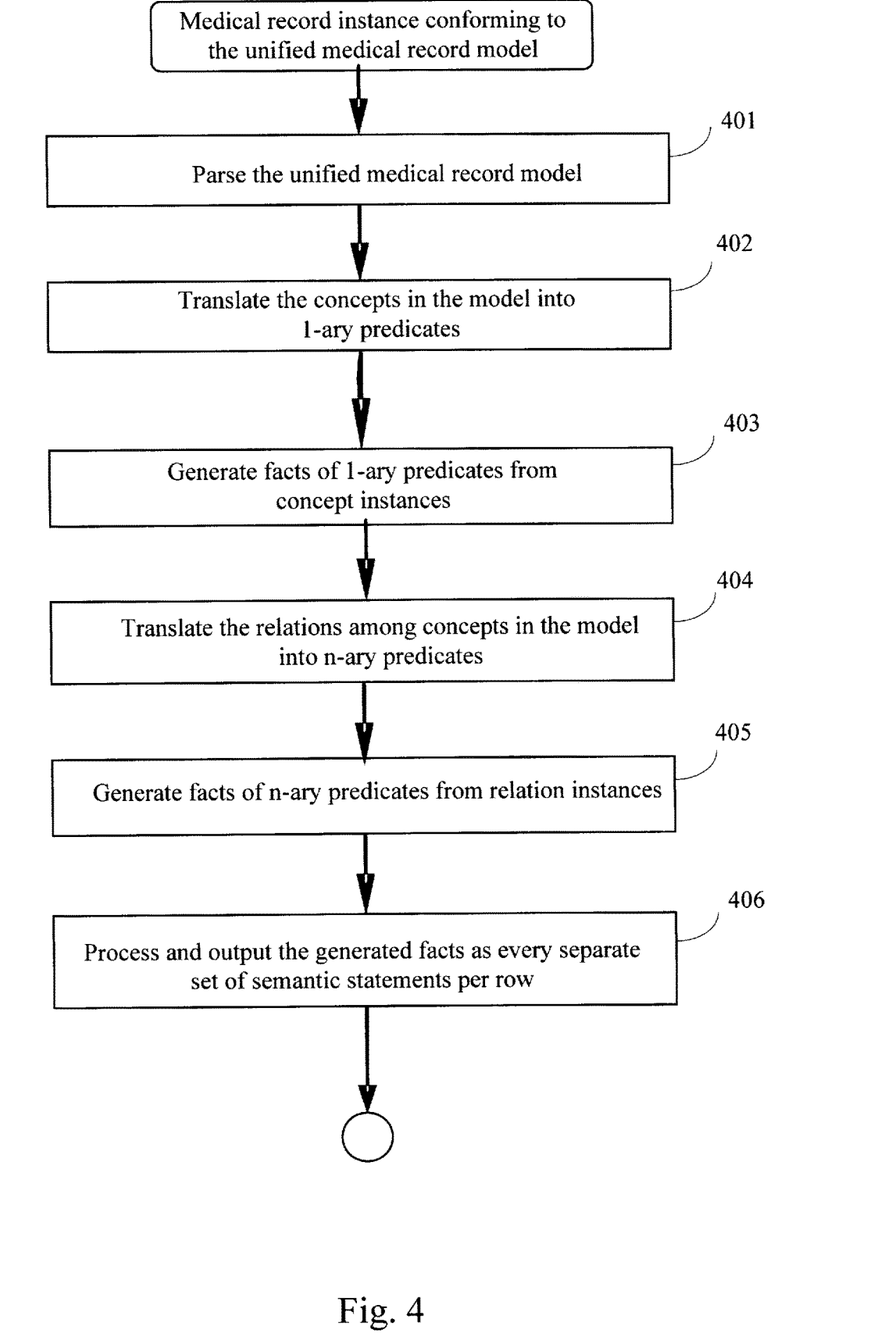
FIG. 4 shows a method for generating temporary facts from a unified medical record model instance of a medical record to be evaluated by a fact generator according to an embodiment of the present invention.

FIG. 4 shows a method for generating temporary facts from a unified medical record model instance of a medical record to be evaluated by the fact generator 102 according to an embodiment of the present invention. The method to generate standard facts from a standard medical record pattern is similar thereto.

As shown in the figure, at step 401, the unified medical record model is parsed.

At step 402, the concepts in the model are translated into 1-ary predicates.

At step 403, facts of 1-ary predicates are generated from the concept instances in the unified medical record model instance of a medical record to be evaluated.

At step 404, relations among concepts in the model are translated into n-ary predicates.

At step 405, facts of the n-ary predicates are generated from relation instances in the united medical record model instance of the medical record to be evaluated.

At step 406, the generated facts are processed and output as every separate set of semantic statements per row.

For example, for the unified medical record model instance as shown in FIG. 3, the following temporary facts can be generated:

1: Doc ("clinic medical record"), Section ("chief complaint"), Entry ("entry1"), Contains ("clinic medical record", "chief complaint"), Contains ("chief complaint", "entry1"), SubjectTo ("entry1", "ache"), Symptom ("ache"), FindAt ("ache", "chest"), BodyStructure ("chest").

2: Doc ("clinic medical record"), Section ("chief complaint"), Entry ("entry2"), Contains ("clinic medical record", "chief complaint"), Contains ("chief complaint", "entry2"), SubjectTo ("entry2", "cough"), Symptom ("cough"), Period ("cough", "three weeks"), Time ("three weeks").

The query constructor and executor 103 is used for constructing a query to the knowledge base according to the generated temporary facts, and executing the query by invoking a reasoning engine. The reasoning engine can be any one known in the art or to be developed in the art, such as the existing reasoning engine XSB for logical programming and deductive database system on Unix and Windows, and the reasoning engine Visual Prolog that can support a logical programming language with complex knowledge representation. In an embodiment of the present invention, the query constructor and executor 103 forms the query by negating the temporary facts and union the negated temporary facts with the standard facts in the knowledge base.

Figure 5:
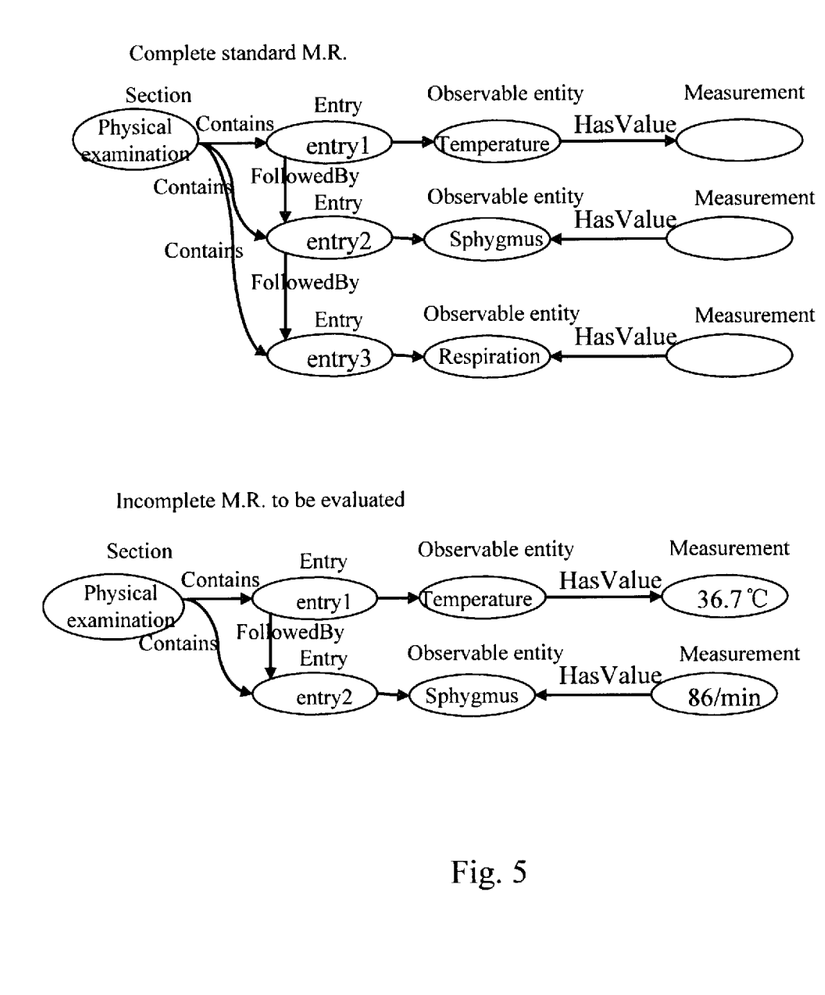
FIG. 5 shows exemplary unified medical record model instances with complete statements and with incomplete statements used in an embodiment of the present invention, respectively.

According to an embodiment of the present invention, the system can be used for identifying incomplete statements in the medical record to be evaluated. For example, compared to the complete statements "physical examination: temperature xx ° C., sphygmus xx/min, respiration xx/min" in a standard medical record, the following statements "physical examination: temperature 36.7° C., sphygmus 86/min" in the medical record to be evaluated are incomplete. FIG. 5 shows the unified medical record model instances with complete statements and with incomplete statements, respectively.

The standard facts generated by the complete statements in the standard medical record and stored in the knowledge base are as follows:

Section("physical examination"), Entry("entry1"), ObservableEntity("temperature") . . . .

Section("physical examination"), Entry("entry2"), ObservableEntity("sphygmus") . . . .

Section("physical examination"), Entry("entry3"), ObservableEntity("respiration") . . . .

The temporary facts generated by the incomplete statements in the medical record to be evaluated are as follows:

Section("physical examination"), Entry("entry1"), ObservableEntity("temperature") . . . .

Section("physical examination"), Entry("entry2"), ObservableEntity("sphygmus") . . . .

The query constructed by the query constructor and executor 103 is as follows:

Query: ?:⌐ [Temporary facts], [Standard Facts]

That is, the temporary facts are negated and then a union is formed with the standard facts. Since the temporary facts lack "Section("physical examination"), Entry("entry3"), ObservableEntity("respiration") . . . " compared to the standard facts, the execution result of the above query will return "Section("physical examination"), Entry("entry3"), ObservableEntity("respiration") . . . ". That is, if the result of the query is not empty, then it can be determined the medical record to be evaluated is incomplete; and if the result of the query is empty, then it can be determined the medical record to be evaluated is equivalent to the standard medical record.

Figure 6:
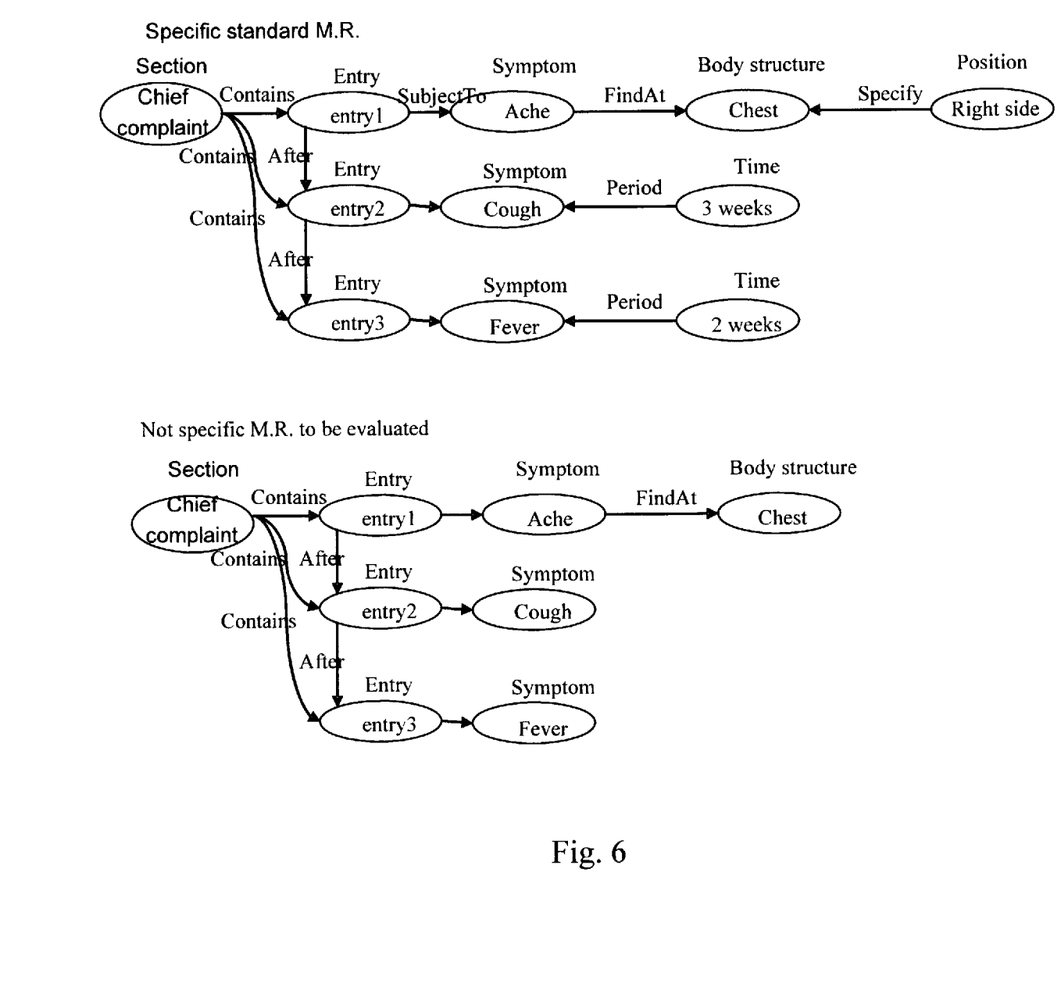
FIG. 6 shows exemplary unified medical record model instances with specific statement and with not specific statements used in an embodiment of the present invention, respectively.

According to an embodiment of the present invention, the system can further be used for identifying a not specific statement in a medical record to be evaluated. For example, compared to the specific statements "chief complaint: having an ache at the right side of the chest, having been coughing for three weeks, having a fever for two weeks" in a standard medical record, the following statements "chief complaint: chest ache, cough, fever" in a medical record to be evaluated are not specific enough. FIG. 6 shows the unified medical record model instances with specific statements and with not specific statements, respectively.

The standard facts generated by the specific statements in the standard medical record and stored in the knowledge base are as follows:

... Entry("entry1"), Symptom("ache"), FindAt("ache", "chest"), BodyStructure("chest"), Specify("right side", "chest"), Position("right side") . . . .

The temporary facts generated by the not specific statements in the medical record to be evaluated are as follows:

. . . Symptom("ache"), FindAt("ache", "chest"), BodyStructure("chest") . . . .

The query constructed by the query constructor and executor 103 is as follows:

Query: ? Concept(x):—$_r$ [Temporary facts], [Standard Facts]

That is, the temporary facts are negated, and unioned with the standard facts, and then a necessary target predicate is added. Since the temporary facts lack "Specify("right side", "chest"), Position("right side")" compared to the standard facts, the execution result of the above query will return "Specify("right side", "chest"), Position("right side")".

Namely, if the result of the query is not empty, and includes standard facts in the knowledge base, i.e., the result of the query is not in the temporary facts, then this indicates that the standard facts in the knowledge base include more semantic information, i.e., the medical record to be evaluated is not specific enough compared to the standard pattern; if the result of the query is not empty, and only includes temporary facts, then it indicates the temporary facts already contains all the semantic information in the standard facts, i.e., the medical record to be evaluated is specific enough compared to the standard pattern; and if the result of the query is empty, then it indicates the medical record to be evaluated is equivalent to the standard pattern and thus is as specific.

Figure 7:
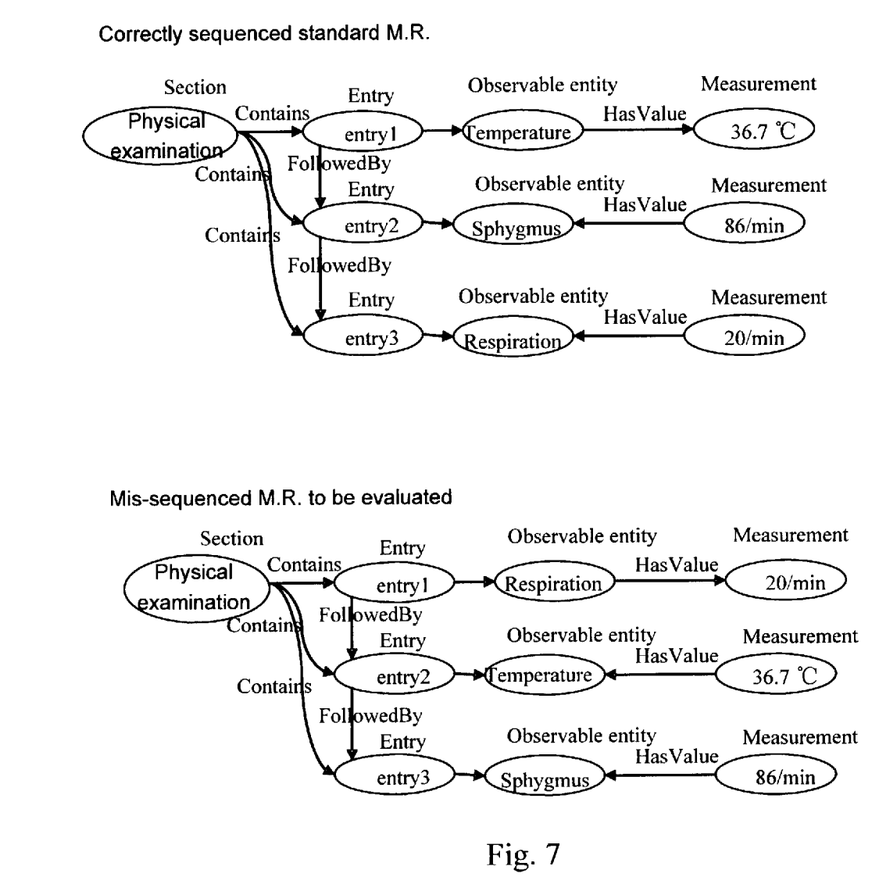
FIG. 7 shows exemplary unified medical record instances with correctly sequenced statements and with mis-sequenced statements used in an embodiment of the present invention, respectively.

According to an embodiment of the present invention, the system can be further used to identify mis-sequenced statements in a medical record to be evaluated. For example, compared to the correctly sequenced statements "temperature 36.7° C., sphygmus 86/min, respiration 20/min" in a standard medical record, the sequence of the statements "respiration 20/min, sphygmus 86/min, temperature 36.7° C." in a medical record to be evaluated are incorrect. FIG. 7 shows the unified medical record model instances with correctly sequenced statements and with the mis-sequenced statements.

The standard facts generated by the correctly sequenced statements in the standard medical record and stored in the knowledge base are as follows:

... FollowedBy("temperature", "sphygmus"), FollowedBy("sphygmus", "respiration"), ObservableEntity("temperature"), . . . .

The temporary facts generated by the mis-sequenced statements in the medical record to be evaluated are as follows:

... FollowedBy("respiration", "temperature"), FollowedBy("temperature", "sphygmus"), ObservableEntity("temperature"), . . . .

The query constructed by the query constructor and executor 103 is as follows:

Query: ? FolllowedBy((x,y): -$_r$ [Temporary facts], [Standard Facts]

That is, the temporary facts are negated and unioned with the standard facts, then a target predicate "FolllowedBy" indicating the sequence relation is added. Since the temporary facts lack "FollowedBy("temperature", "sphygmus"), FollowedBy("sphygmus", "respiration")" compared to the standard facts, the execution result of the above query will return "FollowedBy("temperature", "sphygmus"), FollowedBy("sphygmus", "respiration")". That is, if the result of the query is not empty, then it indicates the sequence of the statements in the medical record to be evaluated is incorrect; and if the result of the query is empty, then it indicates the sequence of the statements in the medical record to be evaluated is correct.

Figure 8:
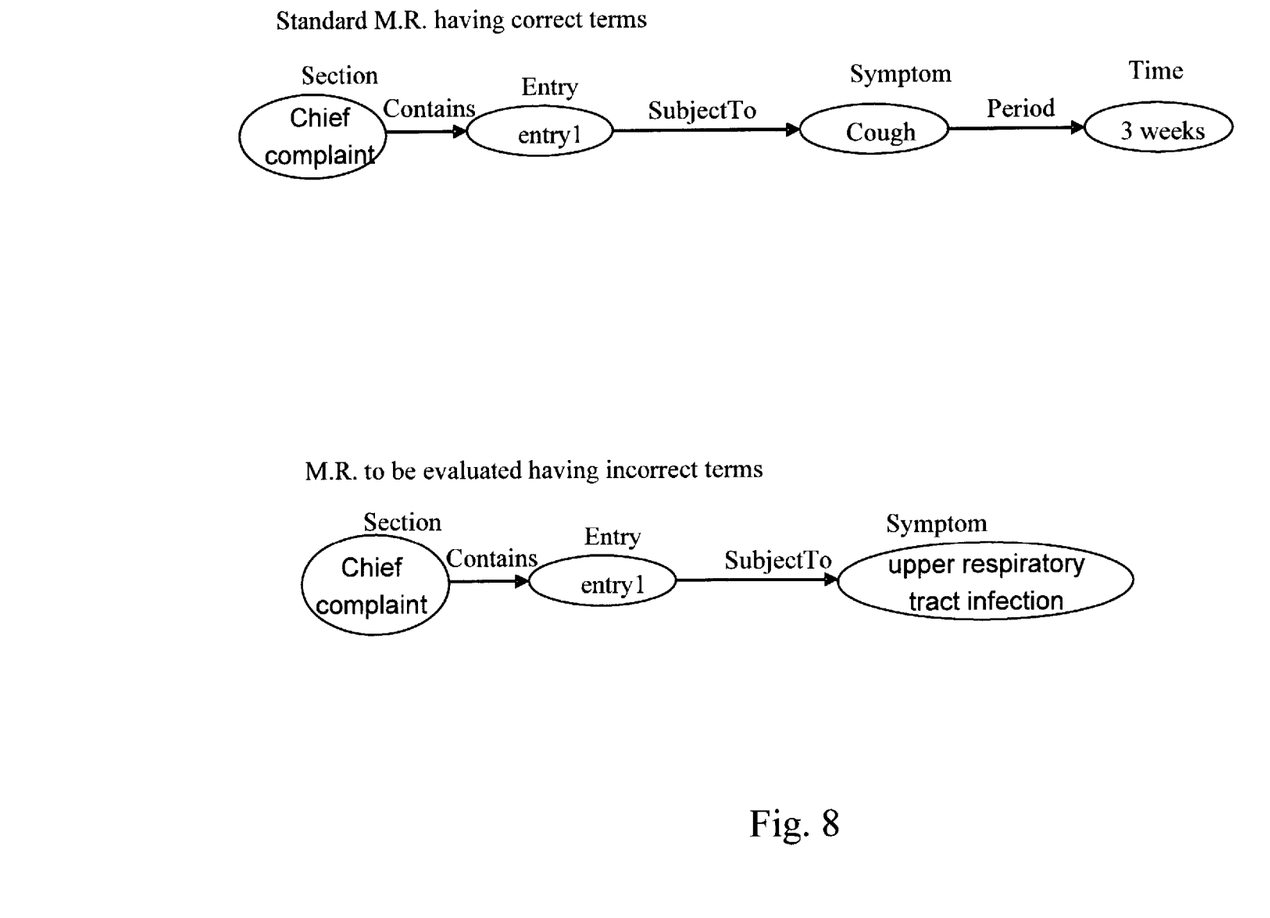
FIG. 8 shows exemplary unified medical record model instances with correct terms and with incorrect terms used in an embodiment of the present invention, respectively.

According to an embodiment of the present invention, the system can further be used to identify incorrect terms in a medical record to be evaluated. For example, compared to the correct terms "chief complaint: having been coughing for three weeks" (description of the symptom) in a standard medical record, the following terms "chief complaint: upper respiratory tract infection" (taking a disease as the chief complaint) are incorrect. FIG. 8 shows the unified medical record model instances with correct terms and with incorrect terms, respectively.

The standard facts generated by the correct terms in the standard medical record and stored in the knowledge base are as follows:

. . . Entry("entry1"), SubjectTo("entry1", "cough"), Symptom ("cough") . . . .

The temporary facts generated by the incorrect terms in the medical record to be evaluated are as follows:

... Entry("entry1"), SubjectTo("entry1", "upper respiratory tract infection"), Disease("upper respiratory tract infection") . . . .

The query constructed by the query constructor and executor 103 is as follows:

Query: ? Concept(z):—$_r$ [Temporary facts], [Standard Facts]

That is, the temporary facts are negated and unioned with the standard facts, and then a necessary target predicate is added. Since the temporary facts lack "Symptom("cough") . . . " compared to the standard facts, the execution result of the above query will return "Symptom ("cough") . . . ". That is, if the result of the query is not empty, then it indicates the temporary facts are not equivalent to the standard fact in the term level, i.e., the medical record to be evaluated uses an incorrect term(s); if the result of the query is empty, then it indicates that the medical record to be evaluated uses the same terms as those in the standard pattern.

While In the foregoing it is described that the system of the present invention can be used for determining four quality problems that a medical record to be evaluated does not comply with a standard medical record, It is obvious to a person skilled in the art that the above four cases are only illustrations, instead of limitation to the present invention. The system of the present invention can also be used to determine other quality problems that a medical record to be evaluated does not comply with a standard medical record.

The query result processor 104 is used to process the result of the querying, thus forming and outputting an evaluation result of the quality of a medical record. The query result processor 104 can process the result of the querying by using methods known by a person skilled in the art; for example, scoring the quality of the medical record to be evaluated based on a certain predefined scoring criterion according to the query result, and outputting the quality evaluation; the query result processor 104 can also directly output the querying result as the quality evaluation result.

While in the foregoing is described the system for automatically evaluating the quality of a medical record, it should be pointed out that the above description is only an illustration instead of limitation to the present invention. The system for automatically evaluating the quality of a medical record of the present invention can have more, less or different modules, and the relationships among the modules can be different from that which is described.

For example, in some embodiments of the present invention, the system can exclude one or more of the universal terminology base 105, the standard medical record pattern base 108, the standard pattern editor 109, the standard pattern generator 110, the quality evaluation rule base 111, the quality evaluation rule editor 112, the medical record semantic annotator 106, the medical record transformer 107; the universal terminology base 105, the standard medical record pattern base 108, the quality evaluation rule base 111 can be incorporated into the knowledge base 101, and so on. All of these variations are within the spirit and range of the present invention.

Figure 9:
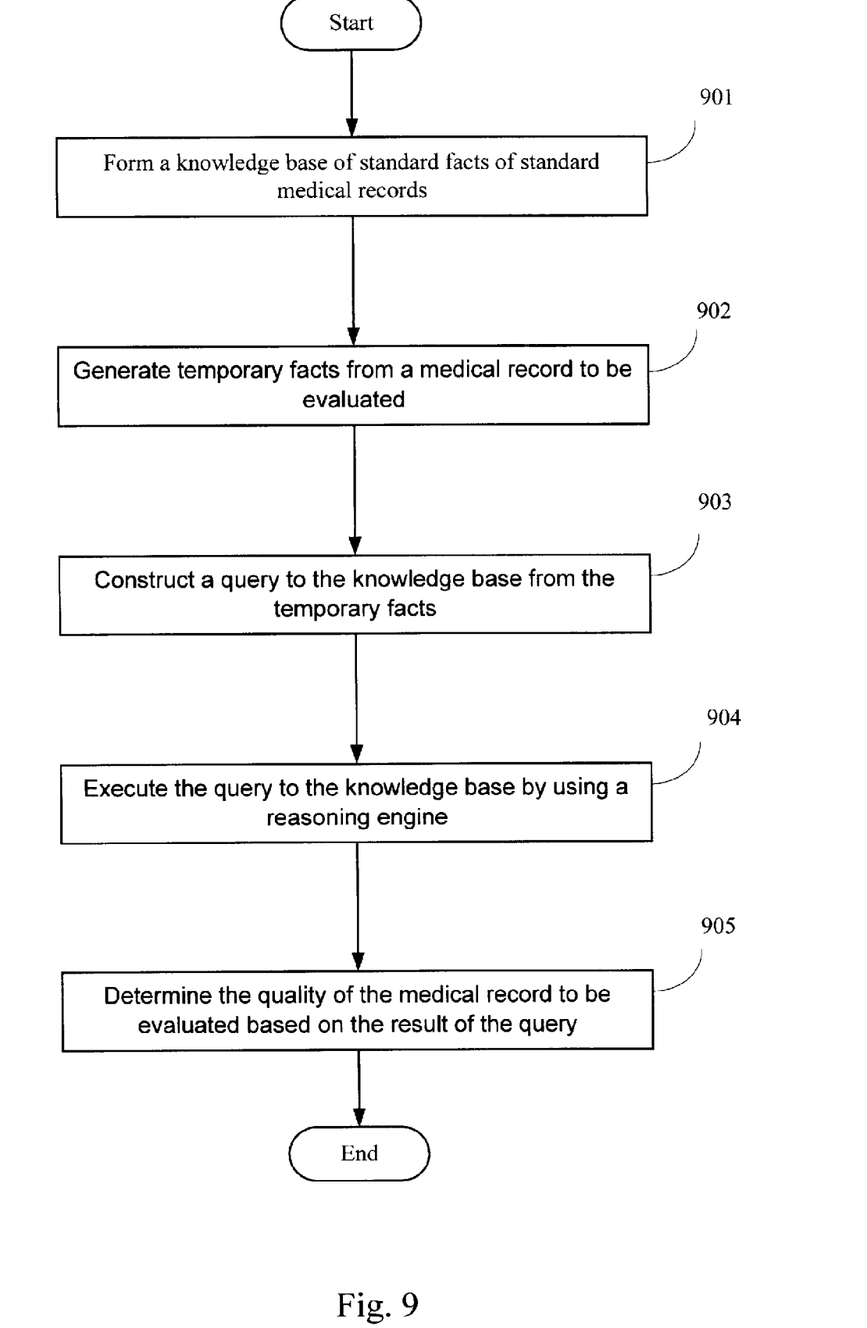
FIG. 9 shows a method for automatically evaluating a medical record according to an embodiment of the present invention.

A method for automatically evaluating the quality of a medical record according to an embodiment of the present invention will be described below with reference to FIG. 9. The method can be implemented by the system for automatically evaluating the quality of a medical record according to the embodiment of the present invention as described above, and can also be implemented by other systems. For the sake of brevity, the same content as those described above will be omitted in the following description. Thus, the method of the present invention described below can be more fully understood by referring to the above description.

As shown in the figure, after the process begins, at step 901, a knowledge base of standard facts of standard medical records is formed.

According to the embodiment of the present invention, the step 901 of forming a knowledge base of standard facts of standard medical records includes the sub-steps of: obtaining a standard medical record pattern; generating standard facts from the standard medical record pattern; and storing the standard facts into the knowledge base.

There, the standard medical record pattern is preferably obtained from a standard medical record pattern base. The standard medical record pattern in the standard medical record pattern base can either be edited by a domain expert manually and stored in the standard medical record pattern base, or be generated automatically by an automatic tool and stored in the standard medical record pattern base.

The sub-step of generating standard facts from a standard medical record pattern is performed by using the same method as that for generating temporary facts from a medical record to be evaluated as described below.

According to an embodiment of the present invention, the step 901 of forming a knowledge base of standard facts of standard medical records further includes the sub-steps of: obtaining a universal terminology base regarding medical records; and obtaining standard facts regarding terms in medical records and their relations from the universal terminology base, and storing them into the knowledge base. In fact, step 901 is optional, since an existing or current knowledge base can be used in the method, without the need to form a relevant knowledge base.

According to an embodiment of the present invention, the step 901 of forming a knowledge base of standard facts of standard medical records further includes the sub-steps of: defining evaluation rules for the quality of medical records; and storing the evaluation rules for the quality of medical records as standard facts into the knowledge base. Preferably, the evaluation rules of the quality of medical records come from a medical record quality evaluation rule base, and the evaluation rules for the quality of medical records in the medical record quality evaluation rule base can either be defined manually by a domain expert and stored in the medical record quality evaluation rule base, or be automatically generated by an automatic tool from standard medical record patterns and stored in the medical record quality evaluation rule base.

At step 902, temporary facts are generated from a medical record to be evaluated.

According to an embodiment of the present invention, the step 902 of generating temporary facts from a medical record to be evaluated includes the sub-steps of: providing semantic annotations to the medical record to be evaluated; and generating temporary facts from the medical record to be evaluated with the semantic annotations.

According to an embodiment of the present invention, the step 902 of forming temporary facts from a medical record to be evaluated includes the sub-steps of: based on a unified medical record model, transforming the medical record to be evaluated into an instance of the unified medical record model; and generating the temporary facts from the instance of the unified medical record model. Therein, the instance of the unified medical record model includes one or more sections, each section includes one or more entries, and each entry includes one or a set of semantically independent statements.

At step 903, a query to the knowledge base is constructed from the temporary facts.

At step 904, the query to the knowledge base is executed through a reasoning engine.

At step 905, the quality of the medical record to be evaluated is determined according to the result of the query.

According to an embodiment of the present invention, the step 903 of constructing a query to the knowledge base from the temporary facts includes the steps of: negating the temporary facts; and forming the union of the negated temporary facts with the standard facts in the knowledge base, thus forming the query. Further, the step 905 of determining the quality of the medical record to be evaluated according to the result of the query includes the step of: when the result of the query is not empty, determining that the medical record to be evaluated is incomplete.

According to an embodiment of the present invention, the step 903 of constructing a query to the knowledge base from the temporary facts further includes the step of: adding a corresponding target predicate to the union of the negated temporary facts and the standard facts in the knowledge base so as to form the query. Further the step 905 of determining the quality of the medical record to be evaluated according to the result of the query includes the step of: when the result of the query is not in the temporary fact, determining the medical record to be evaluated is not specific.

According to the embodiment of the present invention, the step 903 of constructing a query to the knowledge base from the temporary facts further includes the step of: adding a target predicate indicating the sequence of statements to the union of the negated temporary facts and the standard facts in the knowledge base so as to form the query. Further the step 905 of determining the quality of the medical record to be evaluated according to the result of the query includes the step of: when the result of the query is not empty, determining the sequence in the medical record to be evaluated is incorrect.

According to the embodiment of the present invention, the step 903 of constructing a query to the knowledge base from the temporary facts further includes the step of: adding a corresponding target predicate to the union of the negated temporary facts and the standard facts in the knowledge base so as to form the query. Further the step 905 of determining the quality of the medical record to be evaluated according to the result of the query includes the step of: when the result of the query is not empty, determining the medical record to be evaluated contains an incorrect term(s).

While described above is a method for automatically evaluating the quality of a medical record according to an embodiment of the present invention, it should be pointed out that the above description is only an illustration instead of limitation to the present invention. The method for automatically evaluating the quality of a medical record of the present invention can have more, less or different steps, and the sequence among the steps can be different from that which is described. For example, the method can further includes the steps of scoring the quality of a medical record based on the result of the query and a predefined scoring criterion and outputting the scoring result, and so on.

While in the foregoing the present invention is described as a method and system for evaluating the quality of a medical record, the present invention is not limited to the evaluation of the quality of a medical record, and can be used for evaluating the quality of a standardized document of any kind in any industry.

For a detailed description of the method and system for automatically evaluating the quality of a standardized document, refer to the relevant content above.

The present invention can be implemented in hardware, software, or a combination of those. The present invention can be implemented in a single computer system in a centralized mode or in a distributed mode, where, different components are distributed in a number of interconnected computer systems. Any computer system or other apparatus suitable for executing the methods described here is applicable. Preferably the present invention is implemented by a combination of a computer program and general-purpose computer hardware, in which, when the computer program is loaded and executed, it controls the computer system to enable it to execute the method described here, and constitute the system according to the present invention.

The present invention can also be embodied in a computer program product, which includes all the features enabling the methods described here to be executed, and when being loaded into the computer system, can execute the method.

While the present invention is shown and described with reference to the preferred embodiments particularly, a person skilled in the art can understand that various changes both in form and detail can be made without departing from the spirit and scope of the present invention.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A method for automatically evaluating the quality of a medical record, the method comprising:
   providing a knowledge base of standard facts of a standard medical record pattern;
   generating temporary facts from a medical record to be evaluated;
   constructing a query to said knowledge base from said temporary facts, comprising:
      forming a list of the temporary facts and a list of the standard facts;
      removing all facts that are present in both lists; and
      forming a query using remaining standard facts and negations of remaining temporary facts;
   executing said query by a reasoning engine; and
   determining the quality of said medical record to be evaluated using a processor to produce an evaluation result based on said query.

2. The method according to claim 1, wherein generating temporary facts from the medical record to be evaluated comprises:
   providing semantic annotations to the medical record to be evaluated; and
   generating temporary facts from the medical record to be evaluated having the semantic annotations.

3. The method according to claim 1, wherein generating temporary facts from the medical record to be evaluated comprises:
   transforming the medical record to be evaluated to an instance of the unified medical record model; and
   generating the temporary facts from the instance of the unified medical record model.

4. The method according to claim 3, wherein the instance of the unified medical record model comprises one or more sections, each section containing one or more entries, and each entry containing one or a set of semantically independent statements.

5. The method according to claim 1, wherein determining the quality of the medical record comprises:
   determining whether the medical record to be evaluated is incomplete.

6. The method according to claim 1, wherein constructing the query to a knowledge base of standard facts of a standard medical record pattern from the temporary facts further comprises:
   adding a corresponding target predicate to the query, and
   wherein determining the quality of a medical record to be evaluated based on the result of the query comprises:
   determining the medical record to be evaluated not specific when the result of the query is not in the temporary facts.

7. The method according to claim 1, wherein constructing the query to a knowledge base of standard facts of a standard medical record pattern from the temporary facts further comprises:
   adding a target predicate indicating the sequence of statements to the query, and
   wherein determining the quality of a medical record to be evaluated based on the result of the query comprises:
   determining the sequence of statements in the medical record to be evaluated to be incorrect when the result of the query is not empty.

8. The method according to claim 1, wherein constructing the query to a knowledge base of standard facts of a standard medical record pattern from the temporary facts further comprises:

adding a corresponding target predicate to the query, and
wherein determining the quality of a medical record to be evaluated based on the result of the query comprises:
determining the medical record to be evaluated contains incorrect terms when the result of the query is not empty.

9. The method according to claim 1, further comprising:
forming the knowledge base of the standard facts.

10. The method according to claim 9, wherein forming the knowledge base comprises:
obtaining a standard medical record pattern;
generating standard facts from the standard medical record pattern;
storing the standard facts into the knowledge base;
obtaining a universal terminology base regarding medical records;
obtaining standard facts from the universal terminology base regarding the terms in medical records and the relationships thereof; and
storing the standard facts into the knowledge base.

11. The method according to claim 9, wherein forming the knowledge base of standard facts of standard medical records comprises:
defining medical record quality evaluation rules; and
storing the medical record quality evaluation rules as standard facts into the knowledge base.

12. A system for automatically evaluating the quality of a medical records, comprising:
a fact generator for generating temporary facts from a medical record to be evaluated;
a query constructor and executor for constructing a query to a knowledge base of standard facts of a standard medical record pattern from the temporary facts, configured to form a list of the temporary facts and a list of the standard facts, to remove all facts that are present in both lists, and to form a query using remaining standard facts and negations of remaining temporary facts;
a reasoning engine for executing the query to the knowledge base; and
a processor configured to determine the quality of the medical record to be evaluated based on the result of the query.

13. The system according to claim 12, further comprising:
a universal terminology base regarding medical records; and
wherein the knowledge base is further for receiving and storing standard facts regarding terms in medical records and the relationships thereof from the universal terminology base.

14. The system according to claim 12, further comprising:
a medical record semantic annotator for providing semantic annotations to the medical record to be evaluated; and
wherein the fact generator is for generating temporary facts from the medical record to be evaluated having the semantic annotations.

15. The system according to claim 12, further comprising:
a medical record transformer for transforming the medical record to be evaluated into an instance of the unified medical record model; and
wherein the fact generator is for generating the temporary facts from the instance of the unified medical record model.

16. The system according to claim 15, wherein the instance of the unified medical record model comprises one or more sections, each section containing one or more entries, and each entry containing one or a set of semantically independent statements.

17. A computer readable article of manufacture tangibly embodying computer readable instructions for executing a computer implemented method for automatically evaluating the quality of a medical record by a computer, the method comprising:
providing a knowledge base of standard facts of a standard medical record pattern;
generating temporary facts from a medical record to be evaluated;
constructing a query to said knowledge base from said temporary facts, comprising:
forming a list of the temporary facts and a list of the standard facts;
removing all facts that are present in both lists; and
forming a query using remaining standard facts and negations of remaining temporary facts;
executing said query by a reasoning engine; and
determining the quality of said medical record to be evaluated to produce an evaluation result based on said query.

* * * * *